United States Patent
Faram et al.

(10) Patent No.: US 6,663,574 B2
(45) Date of Patent: Dec. 16, 2003

(54) LUNG INFLECTION POINT MONITOR APPARATUS CONNECTION DEVICE

(75) Inventors: Joseph Dee Faram, Dallas, TX (US); Philip E. Fish, Sagle, ID (US)

(73) Assignee: Comedica Technologies Incorporated, Dallas, TX (US)

( * ) Notice: Subject to any disclaimer, the term of this patent is extended or adjusted under 35 U.S.C. 154(b) by 25 days.

(21) Appl. No.: 10/043,000

(22) Filed: Jan. 9, 2002

(65) Prior Publication Data

US 2002/0058879 A1 May 16, 2002

Related U.S. Application Data

(63) Continuation-in-part of application No. 09/575,268, filed on May 22, 2000, now Pat. No. 6,355,002.

(51) Int. Cl.[7] .................................................. A61B 5/08
(52) U.S. Cl. ..................... 600/532; 600/538; 600/529; 128/204.18; 128/205.24
(58) Field of Search .................................. 600/529, 531, 600/532, 533, 538, 537; 128/200.24, 204.18, 204.21, 204.22, 204.23, 205.24

(56) References Cited

U.S. PATENT DOCUMENTS 5,740,796 A * 4/1998 Skog ..................... 128/204.23
5,752,921 A * 5/1998 Orr ............................. 600/533

* cited by examiner

Primary Examiner—Max F. Hindenburg
Assistant Examiner—Navin Natnithithadha
(74) Attorney, Agent, or Firm—John E. Vandigriff

(57) ABSTRACT

A monitor-patient connector used with a lung inflection point monitor for measuring critical opening pressure, over distention pressure, and critical closing of lungs. The monitored-patient connector apparatus is used in conjunction with a lung inflection point monitor, and may be connected to a ventilator breathing circuit. The connector includes a proximal opening for connecting to a patient; a distal end that may be connected to the ventilator breathing circuit, a gas injection port for connecting the connector to a lung inflection point monitor; an isolation valve to prevent gas from entering and escaping during a lung inflection point maneuver; and an exhalation valve for regulating the evacuation of gas from the patient.

9 Claims, 6 Drawing Sheets

LUNG INFLECTION POINT MONITOR APPARATUS CONNECTION DEVICE

This is a continuation-in-part of U.S. application Ser. No. 09/575,268, filed May 22, 2000 now U.S. Pat. No. 6,355,002.

FIELD OF THE INVENTION

The invention relates to a lung inflection point monitor and method, and more particularly to a monitor-patient connector for use with a lung inflection point monitor for measuring critical opening pressure, over distention pressure, and critical closing pressure of lungs.

BACKGROUND OF THE INVENTION

When a patient is ill and requires help breathing, a mechanical ventilator is used. The ventilator typically assists in the breathing process by first delivering a volume of air to the lungs during the inspiratory phase of the breath, and then allowing gas to passively evacuate during the expiratory phase of the breath. During this process gas is exchanged in small air sacks called alveoli. It is in the alveoli that blood becomes oxygenated and expels carbon dioxide, which is, in turn, removed during exhalation.

If a patient is sick enough to require mechanical assistance to breathe, often times a number of alveoli will collapse preventing gas from being exchanged. A goal of the clinician is to re-open these alveoli and keep them open during the ventilation process. The pressure point at which these alveoli open during the inspiratory phase of the breath is called "critical opening pressure." If the critical opening pressure is known, the clinician can program the ventilator so that there is sufficient pressure in the lungs at the end of the expiratory phase of the breath to keep the alveoli from collapsing. This pressure is called "positive end expiratory pressure" or "PEEP."

It is important to know the pressure point at which the lungs again collapse during exhalation. This pressure is referred to as "critical closing pressure." If the critical closing pressure can be ascertained, this pressure point can be correlated to the critical opening pressure allowing the clinician to fine tune the PEEP setting.

As gas is introduced into the lungs during the inspiratory phase of the breath, the lungs continue to expand. If more gas is delivered than the lungs can comfortably accommodate the lungs are stressed and over distend. This "over distention" damages the lungs beginning on a cellular level and may escalate to the point of ripping holes in the lungs. The pressure at which the lungs begin to overfill is referred to as the "over distention pressure." If the over distention pressure is known, the ventilator may be programmed to limit the amount of gas given during the inspiratory phase of the breath by setting a "peak inspiratory pressure" or "PIP" at just below the over distention pressure.

The critical opening pressure, the critical closing pressure and the over distention pressure points are known as "inflections points." By knowing the inflections points, the clinician can program the ventilator to keep the pressures during inspiration and expiration at levels that keep the airways open and prevent over distention. This reduces the risk of injury to the lungs and allows the ventilator to more efficiently ventilate the patient.

The importance of preventing both the collapse and over distention of the lung is well documented. In an article entitled "Open up the lung and keep the lung open" by B. Lachmann, Intensive Care Medicine (1992) 18:319–321, a rationale for preventing airway collapse during ventilation is set forth in order to avoid the dangers concomitant with the pressures required to re-open the airways. The pressure necessary to open collapsed or partially collapsed airways creates dangerous shear forces which can deplete the alveoli of natural surfactant, damage capillaries, decrease compliance, and render gas exchange dysfunctional.

An article entitled "International Consensus Conferences in Intensive Care Medicine: Ventilator-associated Lung Injury in ARDS", which represents a consensus report sponsored by The American Thoracic Society, the European Society of Intensive Care Medicine, the Societe de Reanimation de Langue Francaise utilizing consensus methods established by the National Institutes of Health, asserts that over inflation of the lung induces severe alveolar damage such as alveolar hemorrhage and hyaline membrane disease. The article suggests that ventilator modes associated with properly set PEEP, and delivered tidal volumes which result in a PIP below the over distention point, achieve significant reductions in mortality.

In U.S. Pat. No. 5,937,854, a ventilator pressure optimization method and device is described which attempts to optimize mechanical ventilation by finding the lung inflection points and transmitting this information to the ventilator. The method used involves delivering a known pressure to the patient and measuring the approximate resulting lung volumes. The volumes are then correlated to the delivered pressures and the inflection points are extrapolated. Although this method may provide information helpful in approximating the inflection points, the procedure necessitates measuring lung volume, a costly and difficult maneuver at best. Subsequently, the "approximate" lung volume is used to calculate the "approximate" volume differences as the pressure increases and decreases. These approximate volume differences are used to calculate the inflection points.

U.S. Pat. No. 5,575,283 describes a device for determining the opening pressure of the lungs by trying to measure the delivered lung volumes and trying to establish a relationship between those volumes and delivered pressures. Although different methods are used for trying to establish the lung volumes, the clinician still faces the same difficulties as enumerated in the methodology mentioned above.

U.S. Pat. No. 5,738,090 describes a system for determining the opening pressure of the lung by using a blood gas analyzer to measure partial pressures of oxygen in the blood. When the partial pressure reaches a "predetermined threshold," the threshold is correlated to a pressure that is designated as the opening pressure. However, the partial pressures may or may not be indicative of open airways. The airways may be open, yet still not able to exchange gases due to an underlying pathology of the pulmonary, cardiac, or circulatory system. In addition, the partial pressures may be considered optimal at the very time irreparable, long-term damage is being done to the lungs.

SUMMARY OF THE INVENTION

The present invention is a monitor-patient connector to be used with a lung inflection point monitor for measuring critical opening pressure, over distention pressure, and critical closing pressure of the lungs.

The monitor-patient connector apparatus is used in conjunction with a lung inflection point monitor, and may be connected to a ventilator breathing circuit. The connector includes a proximal opening for connecting to a patient; a distal end that may be connected to the ventilator breathing circuit, a gas injection port for connecting the connector to a lung inflection point monitor; an isolation valve to prevent gas from entering and escaping during a lung inflection point maneuver; and a exhalation valve for regulating the evacuation of gas from the patient.

BRIEF DESCRIPTIONS OF THE DRAWINGS

FIG. 2b shows the backside of the monitor of FIG. 2a;

DESCRIPTION OF A PREFERRED EMBODIMENT

Figure 1A:
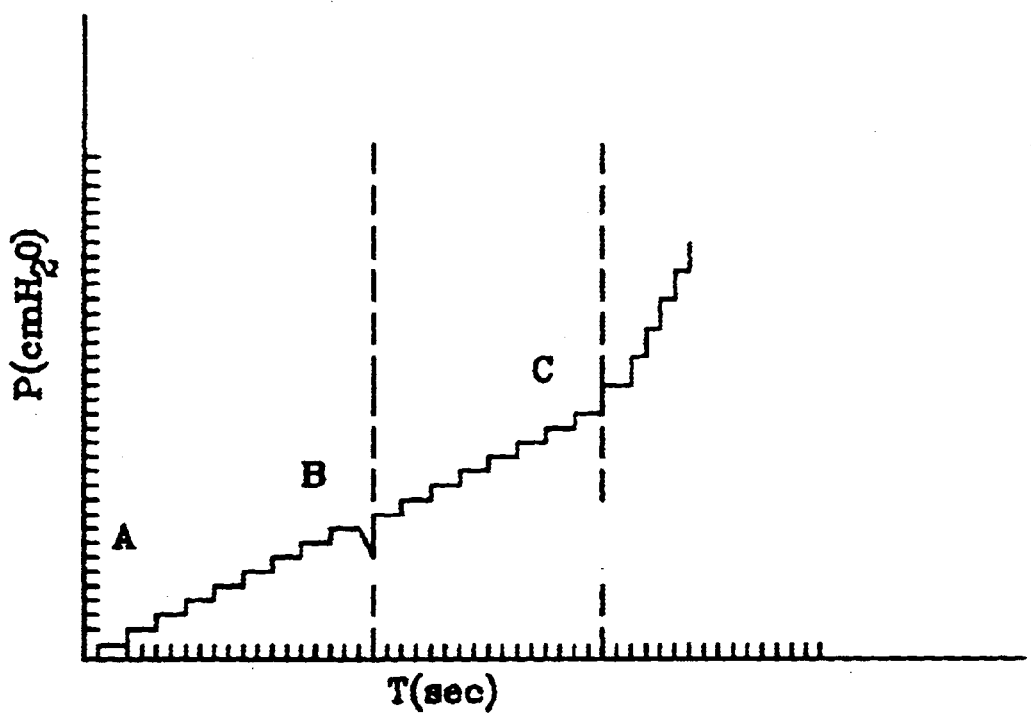
FIG. 1a is a graphic representation of a pressure-time line-graph showing the a-linear pressure points resultant from two of the inflection points of the lungs.

The graphic representation of a pressure-time line-graph shown in FIG. 1 shows incremental pressure increases resultant from pulses of gas delivered to the lung. The pressure in centimeters of water is represented by the vertical axis and the time in seconds, or fractions of seconds, is represented by the horizontal axis. As the pulses of gas are introduced into the lungs the incremental pressure increase is substantially linear from the beginning A to point B. However, at point B the increase becomes momentarily a-linear, showing a drop or a substantial difference in the incremental increase in pressure from one pulse to the next. As the airways, or a significant number of the airways, suddenly open, the lungs are better able to accommodate the volume of gas delivered thereby lowering the pressure within the lungs. When a stepwise pressure increment substantially differs from the previous stepwise pressure increment, this indicates the critical opening pressure.

As the gas continues to be delivered beyond the critical opening pressure B, the pressure increase resumes in a substantially linear fashion until point C. At this time the lung begins to be overfilled resulting in over distention. The graphic increase at point C again becomes a-linear indicating over distention. The higher pressure is caused by the inability of the lung to now adequately accommodate the additional volume resulting in a spike in pressure. This stepwise pressure increment, differing substantially from the previous stepwise pressure increment, indicates the over distention pressure point.

Figure 1B:
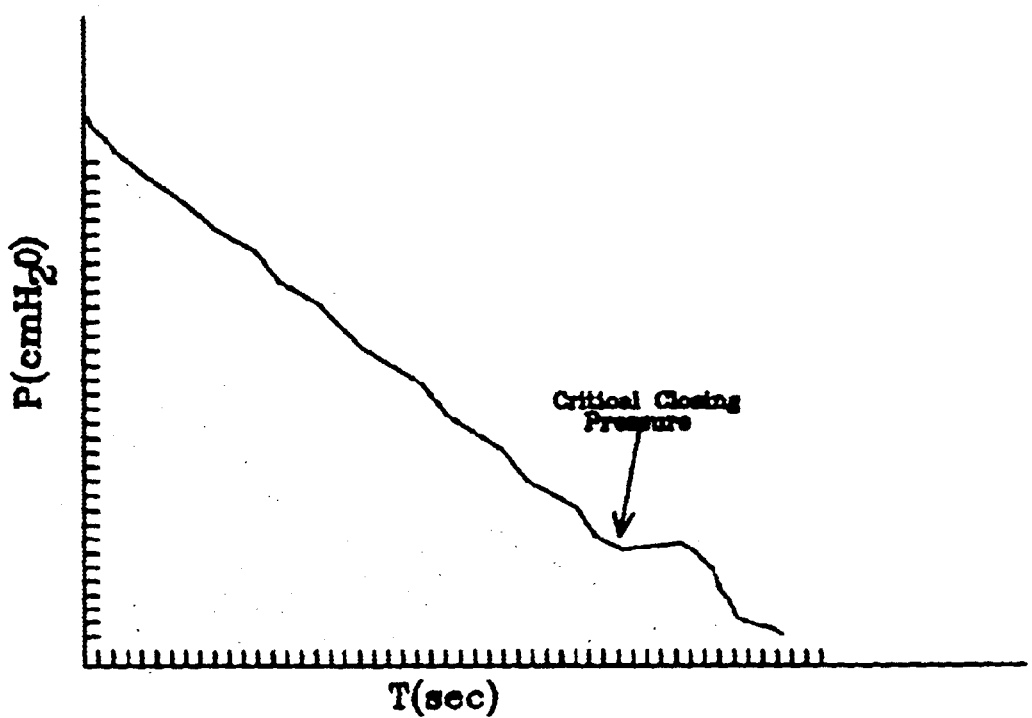
FIG. 1b is a graphic representation of a pressure-time line-graph showing the a-linear pressure point resultant from the critical closing pressure point of the lungs.

FIG. 1b is a graphic representation of a pressure-time line-graph showing the a-linear pressure point resultant from the critical closing pressure point of the lungs.

Figure 2A:
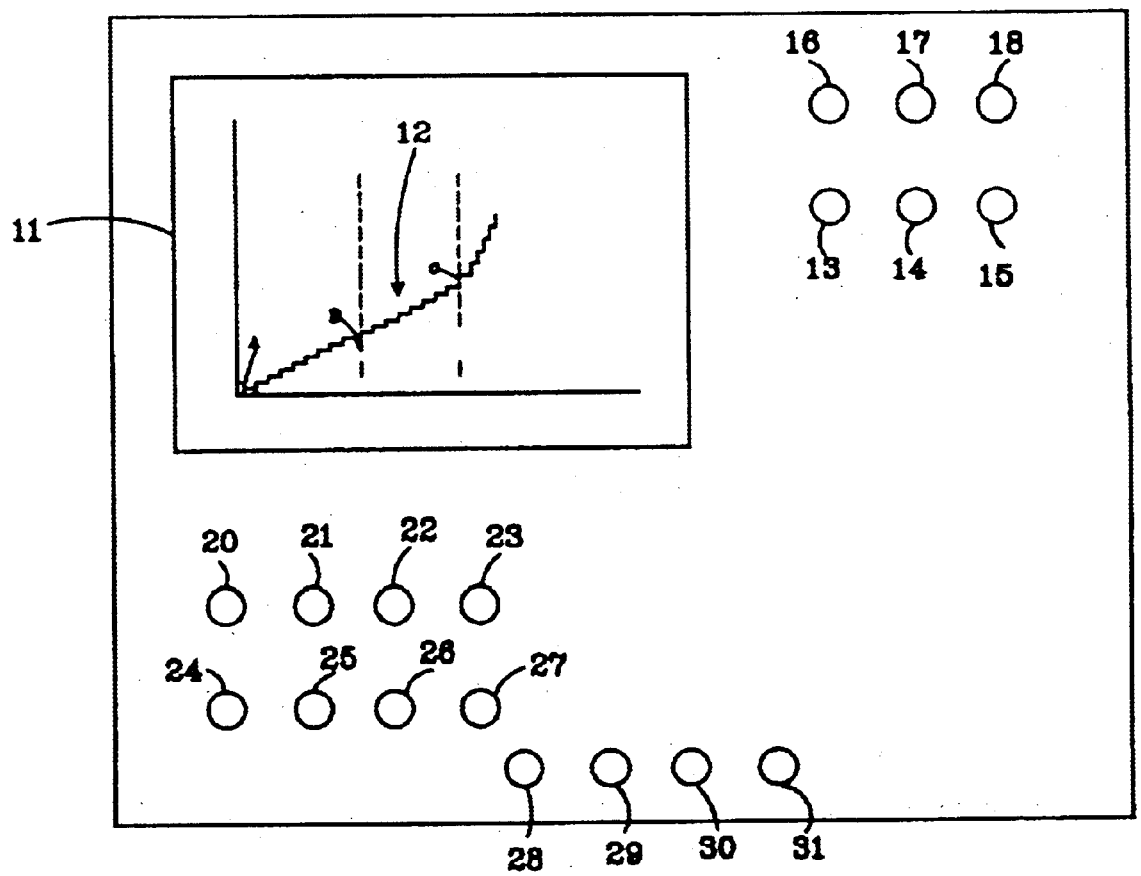
FIG. 2a is a representation of the main unit of the Lung Inflection Point Monitor, which includes the gas-controlling device and the microprocessor for measuring, analyzing, displaying and transmitting data.

FIG. 2a shows the front panel of the Lung Inflection Point Monitor 10. The top half of unit 10 depicts an electronic graphic display module 11 which displays a pressure-time line 12. Pressure is represented by the vertical axis and time is represented by the horizontal axis. This is similar to the graphical display of FIG. 1a. Graphics display module 11 may be, for example, a VDR Monitron® Wave Form Analyzer manufactured by Percussionaire® Corporation of Idaho. The sensitivity or amplitude of the pressure increments is adjustable by control 13 and the sweep speed time is adjustable by control 14. The waveform monitor can be connected to a printer to print out the graphical waveform by pushing print button 15. To adjust high and low alarms, controls 16 and 17 are used. Controls 16 and 17 may be connected to the microprocessor and modified to initiate and terminate the maneuver at pre-set parameters. The device is turned on and off by a switch 18. A microprocessor within the device may be programmed for the purpose of analyzing the data measurements and transmitting information and commands to a gas-controlling device and to a ventilator.

Controls for monitor 10 are shown at the bottom half of FIG. 2a. These controls allow the clinician to control the inflection point maneuver. A gas injection port 28 connects to one end of a tube (⅛" ID) for the purpose of delivering the pulsatile flow of gas to the patient. The other end of the tube connects to the patient via a monitor-patient interface described below. An isolation valve port 29 connects to one end of a tube (⅛" ID) for the purposes of opening and closing a valve on the inspiratory branch of the monitor-patient interface. An exhalation valve port 30 connects to one end of a tube (⅛" ID) for the purpose of opening and closing a valve on the expiratory branch of the monitor-patient interface. A proximal pressure port 31 connects to one end of a tube (⅛" ID) for the purposing of sampling lung pressure. The other end of this tube is connected to the monitor-patient interface and samples gas proximally either internal or external to the oral cavity of the patient. A button 24 closes the exhalation valve on the expiratory limb of the monitor patient interface and a button 25 opens the exhalation valve on the expiratory limb of the monitor-patient interface. A button 26 closes the isolation valve on the inspiratory limb of the monitor-patient interface and a button 27 opens the isolation valve on the inspiratory limb of the monitor-patient interface. An expiratory valve adjustment knob 20 allows the clinician to partially close the exhalation valve on the expiratory limb of the monitor-patient interface. A flow-timing knob 21 allows the clinician to control the time ratio of the "flow" portion of the pulse of gas during the pulsatile delivery. A no-flow-timing knob 22 allows the clinician to control the time ratio of the "no-flow" portion of the pulsatile gas delivery. A pulse rate knob 23 allows the clinician to control the number of pulses per minute delivered during the pulsatile delivery of gas.

Figure 2B:
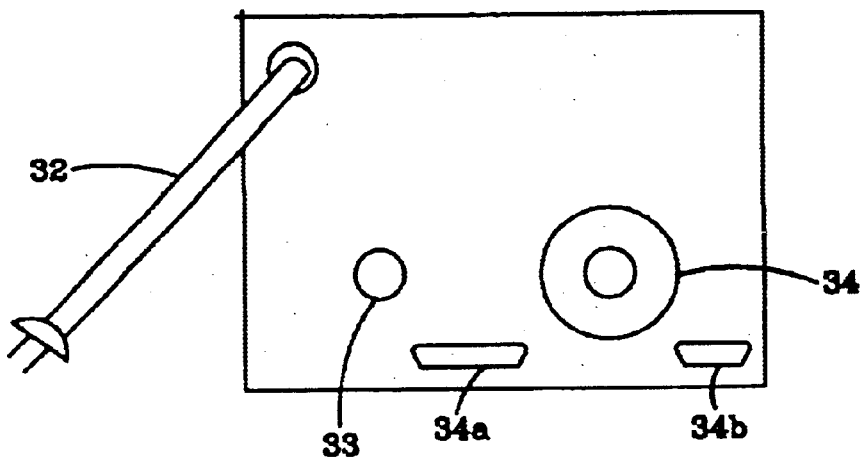

FIG. 2b shows the back of the main unit with a power cord 32, a source gas connection 33, a pressure regulator control knob 34, a printer connection port 34a, and a serial port 34b for connecting to a ventilator.

Figure 3A:
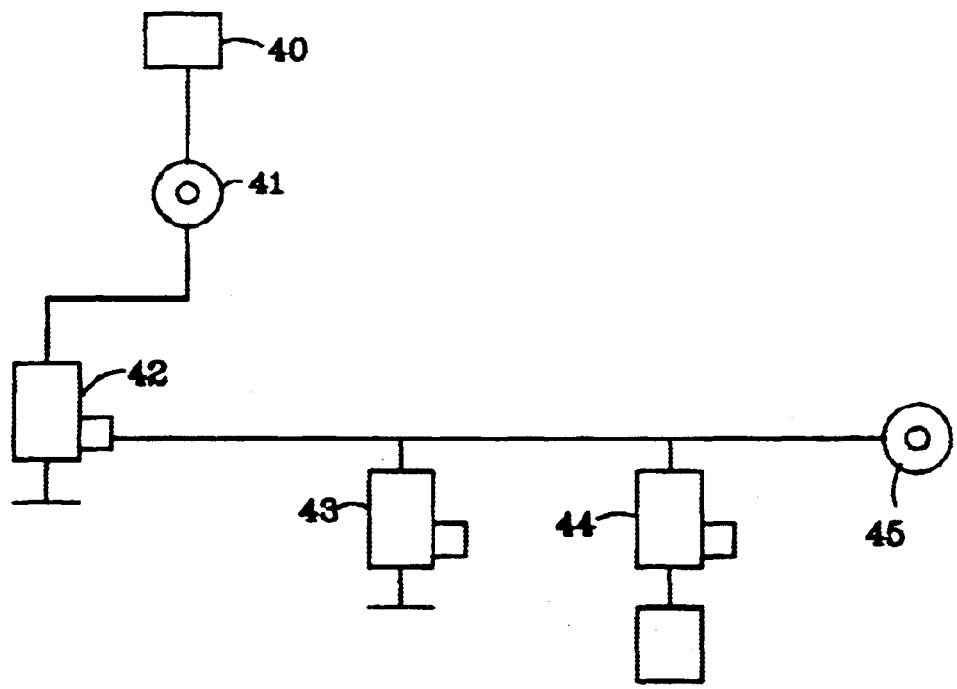
FIGS. 3a and 3b are schematic representations of a portion of the gas-controlling device.

FIG. 3a is a schematic representation of the controlling mechanism for the exhalation valve. Unless otherwise stated, each element described herein is connected by flexible tubing (⅛" ID). The 50 p.s.i source gas 40 connects to a reduction regulator 41. The reduction regulator 41 connects to a 2-way push button valve 46 which, when pushed, sends gas through to the exhalation valve 45 in order to close the valve. Located in line between push button valve 42 and exhalation valve 45 are two more valves. A push button valve 43 opens the line to the exhalation valve 45 resulting in the complete opening of the valve. Adjustable valve 44 is located in-line between push button valve 43 and exhalation valve 45. The adjustable valve 44 allows the clinician to partially open the exhalation valve during the maneuver. A complete duplicate of this schematic is used for the isolation valve.

Figure 3B:
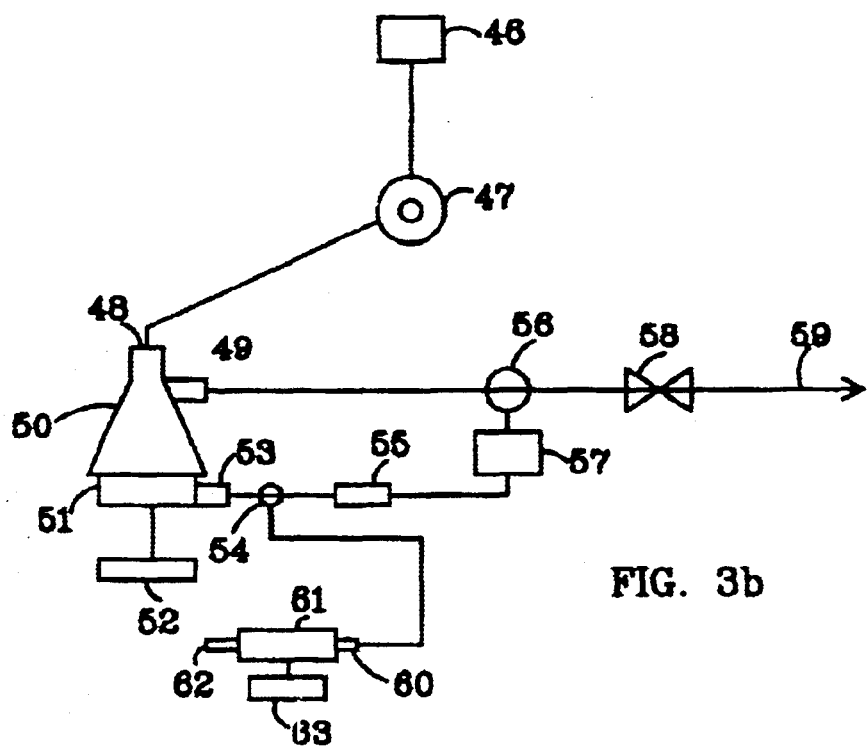

FIG. 3b is a schematic representation of the controlling mechanism for the pulsatile gas injection. A source gas 46 is connected to a reduction regulator 47. The reduction regulator sends gas to the front inlet port 48 of a flow-interrupting cartridge 50 of known construction, such as part number 00216 manufactured by Bird Corporation of Palm Springs, Calif. The gas passes through an open valve in the cartridge, through the cartridge outlet port 49 where it continues toward the patient through a bleed-off port 56, then through a flow-metering valve 58, and then to the monitor-patient interface 59 where it is delivered to the patient. The amount of gas which bleeds off through port 56 is directed through a 0.023 reduced orifice 57 and then continues through a one-way check valve 55. From one-way check valve 55, the gas proceeds through another bleed-off port 54 as it continues to the back inlet port 53 of the flow-interrupting cartridge 50 where it re-enters through a manifold 51. A metering valve 52 allows the flow back into the manifold 51 to be calibrated. As the flow re-enters the cartridge 50, it overwhelms a diaphragm within the cartridge, pushing the valve closed, which interrupts the flow. As the flow coming through the front inlet port 48 builds up pressure, it again pushes the valve open and process begins anew. The gas, which bleeds off through port 54, is directed into the inlet port 60 of an adjustable orifice valve 61 and exits into the atmosphere through outlet port 62. The orifice valve 61 is adjusted by metering valve 63.

This preferred embodiment utilizes pneumatic logic for controlling the pulsatile delivery of gas and controlling all of the valves, although it could easily be done electronically.

Figure 4A:
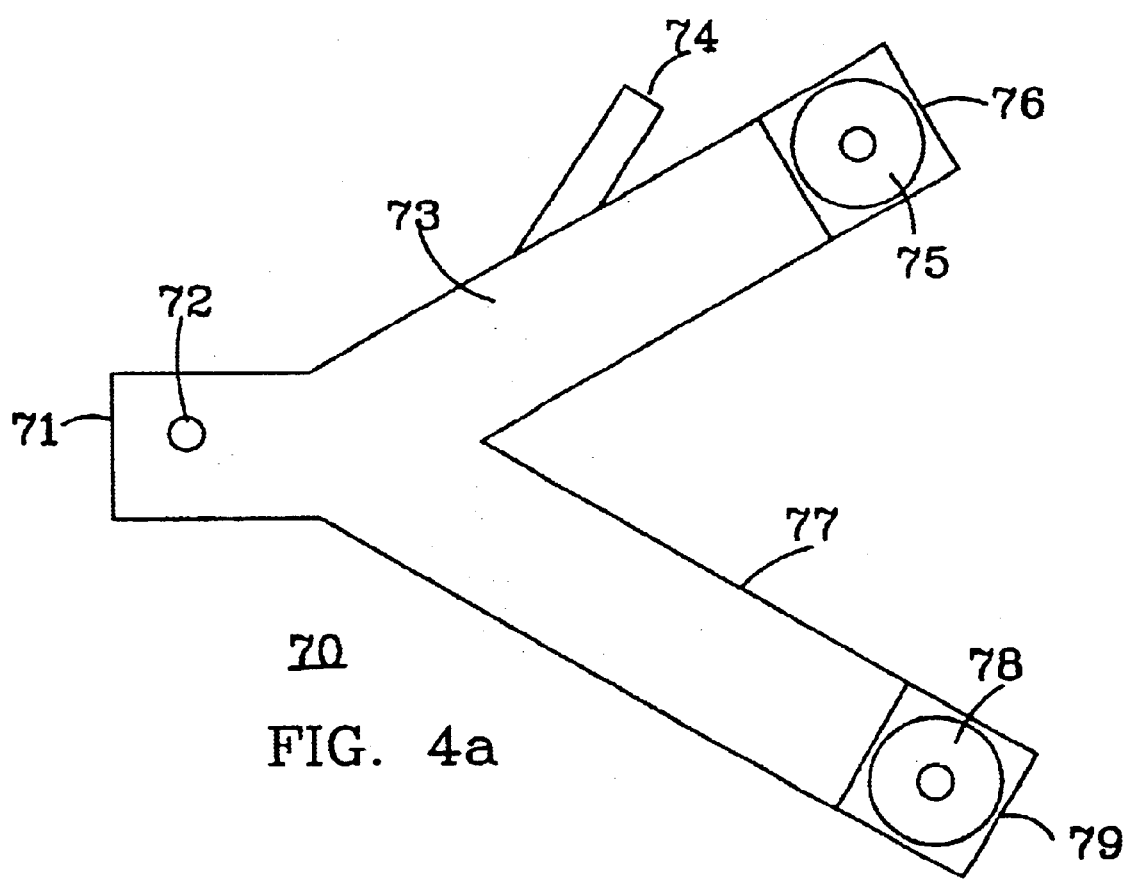
FIGS. 4a, 4b, 4c and 4d are examples of several embodiments of the monitor-patient interface connector.

FIG. 4a shows one embodiment of the monitor-patient connector 70 configured in a "Y". The monitor-patient connection 70 is constructed of a non-compliant material in order to prevent pressure fluctuations from being caused by any portion of the device. The monitor-patient connector has a proximal opening 71 designed to connect to the patient airway, such as an endotrachael tube. Next to opening 71 is a proximal pressure port 72 to which one end of a proximal pressure line is connected, and the other end of the line is connected to port 31 on the front panel of the main unit. One branch of the "Y" is the inspiratory branch 73 on which is located a gas injection port 74. One end of a tube is connected to port 74 and the other end of the tube is connected to port 28 on the front panel of monitor 10. An isolation valve 75, upon closing, will serve to isolate the maneuver from gas either entering or escaping the monitor-patient connector. The inspiratory branch opens distally with a connector 76 designed to fit onto the inspiratory branch of a ventilator breathing circuit. Another branch of the "Y" is the expiratory branch 77. Exhalation valve 78, upon closing, serves to prevent gas from either entering or escaping during the maneuver. The exhalation valve can be partially closed during exhalation. On the distal end of the expiratory branch 77 is a connector 79 designed to fit onto the expiratory branch of a ventilator breathing circuit. This embodiment is designed such that the inflection point maneuver may be done either by leaving the monitor-patient connector in-line in the ventilator breathing circuit, or the patient may be taken off the ventilator circuit before the maneuver and placed back on afterwards.

Figure 4B:
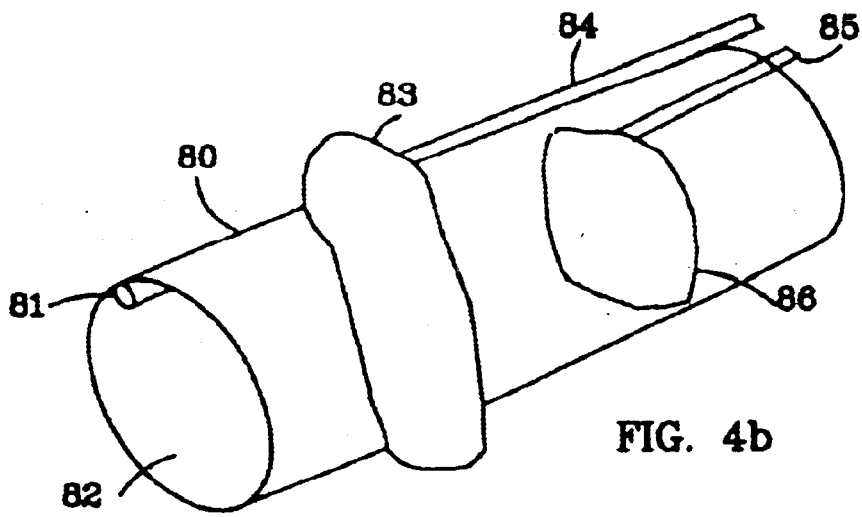

FIG. 4b shows an embodiment of the monitor-patient connector where the monitor-patient connector is incorporated into the patient airway of an endotrachael tube 80 and becomes part of the endotrachael tube. The endotrachael tube 80 is placed by the clinician into the trachea of the patient and opens at 82 into the trachea. Gas may be injected through tube 81. An external cuff 83 is then inflated via tube 84 by the clinician in order to prevent the escape of gas around the outside of the endotrachael tube. Another tube 85 connects to an internal exhalation valve balloon 86. Gas is injected into the exhalation valve balloon 86 via tube 85 in order to prevent gas from either escaping or entering the airways during the maneuver. The exhalation valve balloon 86 can be partially closed during exhalation. In this embodiment the internal exhalation valve balloon 86 serves also as the proximal pressure measuring device. As pressure increases in the airways more pressure is transferred to the balloon 86, which, in turn, transmits pressure via tube 85 back to the main unit.

Figure 4C:
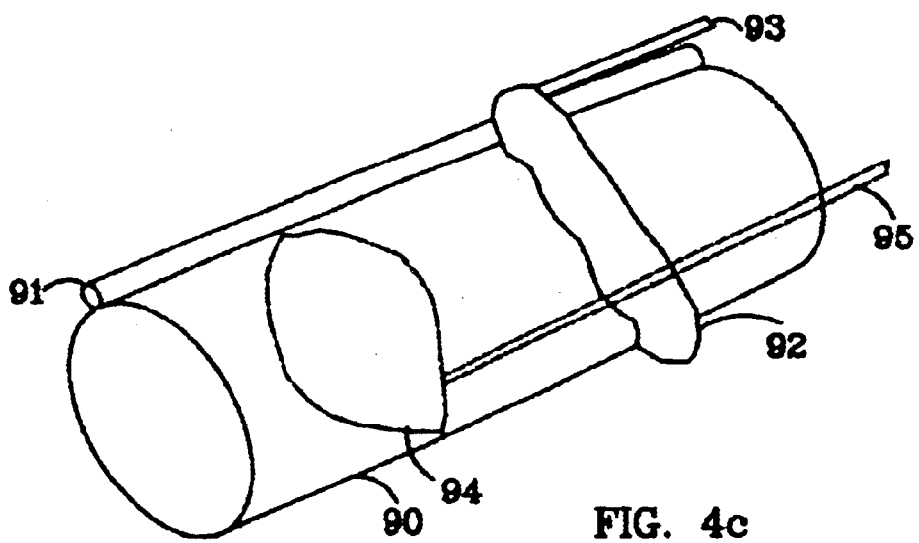

In FIG. 4c, endotracheal tube 90 shows the tube opening again into the trachea with the injection tube 92 being placed on the external portion of the endotrachael tube. Gas may be injected through tube 91. The external cuff 92 prevents gas from passing on the outside of the endotrachael and is filled through tube 93. Internal exhalation valve balloon 94 is filled through tube 95. Internal exhalation valve balloon 94 also serves as a pressure measuring device, transferring airway pressure to the main unit via tube 95. The exhalation valve balloon 94 can be partially opened upon exhalation.

Figure 4D:
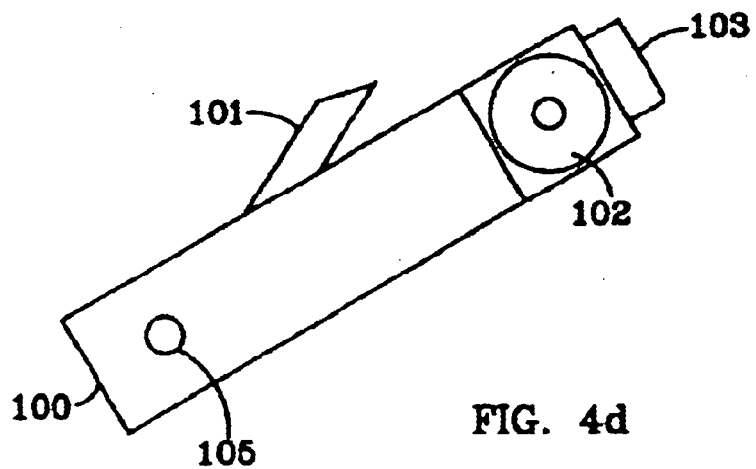

Another embodiment (FIG. 4d) of the monitor-patient connector is a simple straight connector. The proximal end 100 is designed to fit onto a patient airway, such as an endotrachael tube. The gas injection port 101 connects to one end of a tube, whose other end connects to the front panel of main unit 10. The exhalation valve 102 serves the purpose of preventing gas from entering or escaping during the maneuver, and may also be partially opened upon exhalation. Distal end 103 is designed to connect to a ventilator breathing circuit. There is a proximal pressure point opening 105 adjacent to the proximal end 100. This embodiment may be used either with or without the patient being connected to the ventilator breathing circuit.

To begin the inflection point maneuver the Lung Inflection Point Monitor is prepared for the maneuver by plugging the power cord 32 into a grounded electrical outlet and connecting to a 50 p.s.i. gas source 33. The pressure reduction regulator 34 is set to the desired operating pressure in order to produce the desired flow. A printer may be connected to printer port 34a on monitor 10, and a ventilator may be connected to the serial port 34b. The monitor 10 is turned on, amplitude levels are set by adjusting the sensitivity knob 13, and the sweep speed is set by adjusting the sweep knob 14 in order to best view the display.

The pulsatile delivery of gas consists of two parts: 1) flow and 2) no-flow. The ratio of flow to no-flow is adjusted to the desired setting by adjusting the flow-timing knob 21 and the no-flow-timing knob 22. The rate of delivered pulses is adjusted to the desired level by turning the pulse rate knob 23.

After the Lung Inflection Point Monitor is set up, the maneuver begins by immobilizing the patient's lungs. This may be done with a paralytic drug such as Respironium®, which is very short lasting paralytic developed for this purpose. Any method may be utilized to assure that the lungs do not move during the maneuver. If there is any thoracic movement, pressure readings may not be reflective of the condition of the lungs and the inflection point measurements may be distorted. Next, both the exhalation and isolation valves are closed in order to control both the entry and escape of gas during the inflection point maneuver.

Gas is then delivered in pulsatile increments into the patient's lungs starting at a pressure below the critical opening pressure. As the pulses build up, pressure in the lungs is graphically displayed in the form of a pressure-time line on the monitor screen 11 and continues to escalate. As the alveoli, or a significant number of alveoli, open there is an a-linear movement in the line-graph. As the pressure is increased on an alveolus that is essentially deflated, a critical opening pressure will be reached. The pressure required to open an alveolus is relative to both the surface tension and the radius of the collapsed alveolus. Especially in a situation where the alveolus is depleted of natural surfactant, which has the ability to vary the surface tension, the pressure required to open the alveolus may be relatively high. This is expressed in the Laplace Law, $P=2\,T/r$, where P is pressure, T is surface tension and r is radius.

When the critical opening pressure is reached, the alveolus very rapidly inflates. After the alveolus is inflated, less pressure is then required to keep it open. This is represented on the pressure-time line as a decrease in the pressure, causing the line increase to become a-linear. This a-linear movement will, in turn, be followed by a decrease in the pressure rise from each pulsatile increment of gas. This is expressed by Boyle's formula, Flow×Time initial/Pressure initial=Flow final×Time final/Pressure final. This a-linear movement seen in the pressure-time line is caused when a stepwise pressure increment substantially differs from the previous stepwise pressure increment, thereby indicating the critical opening pressure. The critical opening pressure is displayed 11.

As the pulsed gas continues to build pressure in the lungs, eventually the elastic limits of the lung will be reached and the lungs start to over distend. This will be represented on the pressure-time line by a rise in the pressure of each pulsatile increment as compared to the increment immediately preceding, and as defined again by the formula Flow×Time initial/Pressure initial=Flow final×Time final/Pressure final.

This is shown on the pressure-time line as an a-linear movement. As a stepwise pressure increment substantially differs from the previous stepwise pressure increment, the over distention pressure is indicated. That pressure is displayed 11.

After the over distention point is reached, the introduction of gas into the patient's lungs is discontinued by turning knob 23, and the exhalation valve is partially opened with knob 20 in order to allow gas to escape from the lungs and to monitor the resulting pressures. As the alveoli, or a significant number of alveoli, collapse the pressure time line will show an a-linear movement indicating the critical closing pressure. That pressure is displayed 11.

Upon completion of the maneuver, both the exhalation valve 78 (FIG. 4a) and the isolation valve 75 are opened completely in order to re-establish the connection with the ventilator circuit. The PEEP and the PIP are set on the ventilator, either manually by the clinician, or automatically by the Lung Inflection Point Monitor microprocessor, in order to optimally ventilate the patient.

Figure 5:
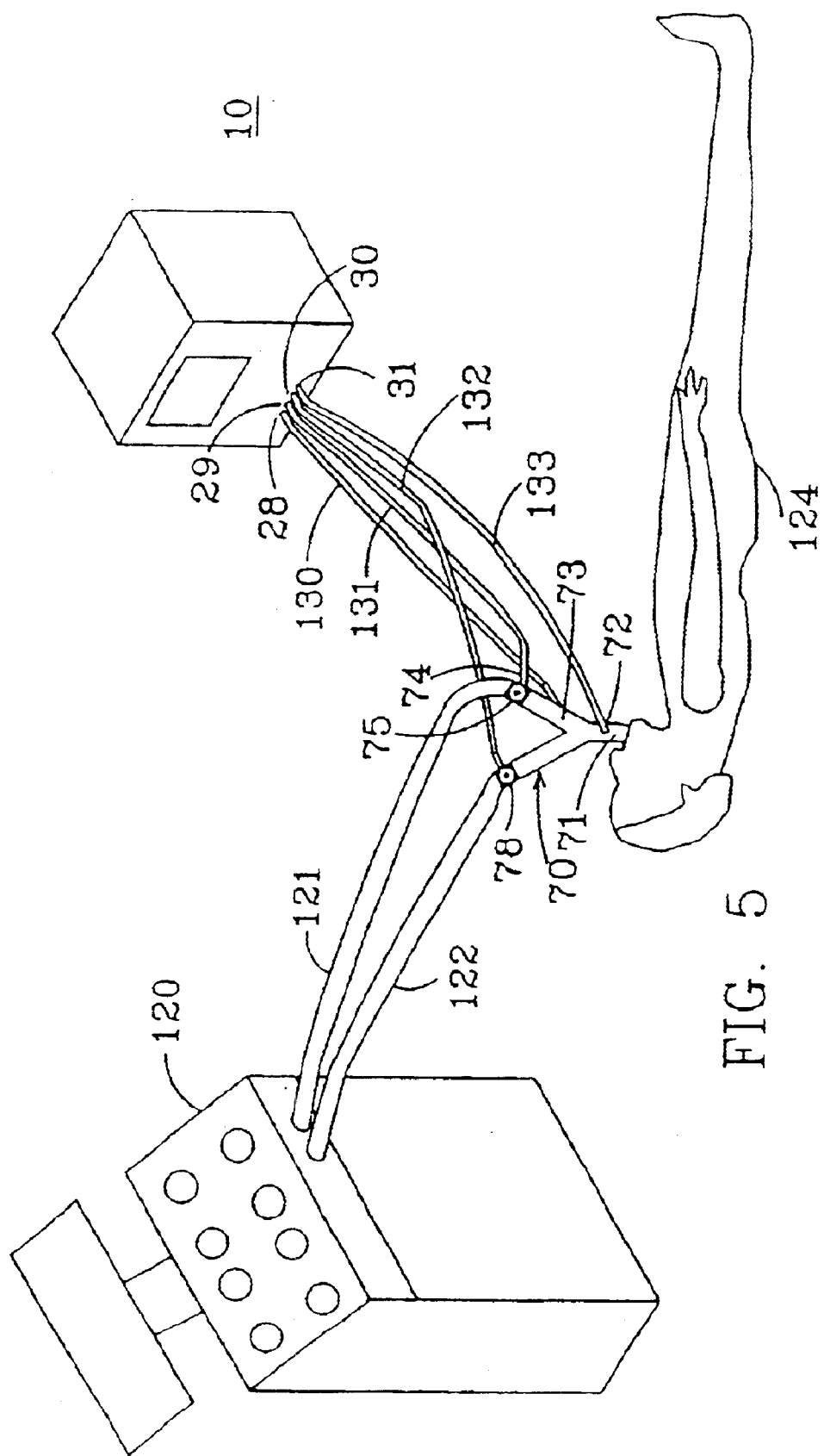
FIG. 5 shows a patient connected to a ventilator 120 and a Lung Inflection Point Monitor 10 using the monitor-patient interface connector.

FIG. 5 shows a patient connected to a ventilator 120 and a Lung Inflection Point Monitor 10. A monitor-patient connector 71 serves as a part of the ventilator circuit 121 and 122, and has the ability to isolate the patient from the ventilator 120 during the inflection point monitor maneuver. The monitor-patient connector 70 is connected to the monitor 10 by four tubes, 130, 131, 132 and 133. Tube 130 connects by one end to the gas injection port 74 of the monitor-patient connector and by the other end to the gas injection outlet port 28 of the monitor. Tube 131 connects by one end to the isolation valve 75 of the monitor-patient connector and by the other end to the isolation valve port 29 of monitor 10. Tube 132 connects by one end to the expiratory valve 78 of the monitor-patient connector and by the other end to the expiratory valve port 30 to monitor 10. Tube 133 connects by one end to the proximal pressure port 72 of the monitor-patient connector and by the other end to the proximal pressure port 31 of monitor 10. The Lung Inflection Point Monitor 10 consists of a module which measures, analyzes, displays and transmits data, and a module which controls the delivery of gas to the patient, as well as the opening and closing of exhalation and isolation valves.

What is claimed:

1. A monitor-patient connector for use with a lung inflection point monitor for measuring critical opening pressure, over distention pressure, and critical closing pressure of lungs, said connector including:
   a proximal opening for connecting to a patient;
   a pressure measuring port, located in a proximal common flow area of the connector that conducts both ingress and egress of gas during respirator treatment;
   a gas injection port for connecting the connector to a lung inflection point monitor; and
   at least one isolation/exhalation valve to prevent respirator treatment gas from entering the patient's lungs and to prevent lung inflection point maneuver gas from escaping the patient's lungs during the gas injection phase of the lung inflection point maneuver, and to control the egress of gas during the gas evacuation phase of the lung inflection point maneuver.

2. The monitor-patient connector according to claim 1, wherein said isolation/exhalation valve is a structure within the connector.

3. The monitor-patient connector according to claim 2, wherein said valve structure is also used to measure airway pressure.

4. The monitor-patient connector according to claim 1, including a distal end for connecting to a ventilator breathing circuit.

5. The monitor-patient connector according to claim 1, wherein an external cuff is used on the connector to prevent the escape of gas around the outside of the connector.

6. The monitor-patient connector according to claim 5, wherein said cuff is also used to measure airway pressure.

7. The monitor-patient connector according to claim 1, wherein said connector has a gas injection tube mounted thereon.

8. A monitor-patient connector for use with a ventilator breathing circuit used in conjunction with a lung inflection point monitor for measuring critical opening pressure, over distention pressure, and critical closing pressure of the lungs, said connector including:
   a proximal opening for connecting to a patient;
   a pressure measuring port located in a proximal area of the connector that conducts both ingress and egress of gas during respirator treatment;
   a gas injection port for connecting the connector to a lung inflection point monitor;
   at least one isolation/exhalation valve to prevent respirator treatment gas from entering the patient's lungs and lung inflection point maneuver gas from escaping the patient's lungs during the maneuver, and to control the escape of gas during the exhalation phase of the maneuver; and
   an interface means for connecting the ventilator breathing circuit used in conjunction with the lung inflection point monitor.

9. A monitor-patient connector for use with a ventilator breathing circuit used in conjunction with a lung inflection point monitor for measuring critical opening pressure, over distention pressure, and critical closing pressure of lungs, said connector including:
- a "Y" shaped connector having a proximal opening for connecting to a patient;
- a pressure measuring port located in a proximal area of the connector that conducts both ingress and egress of gas during respirator treatment;
- a first branch of the "Y" shaped connector having a gas injection port for connecting the connector to a lung inflection point monitor, an inspiratory port for connecting to an inspiratory limb of the ventilator circuit, and an isolation valve to prevent respirator treatment gas from entering the patient's lungs and lung inflection point maneuver gas from escaping the patient's lungs during the maneuver; and
- a second branch of the "Y" shaped connector having an expiratory port for connecting to an expiratory limb of the ventilator circuit, and an exhalation valve to prevent respirator treatment gas from entering the patient's lungs and lung inflection point maneuver gas from escaping the patient's lungs during the maneuver, and to control the escape of gas during the exhalation phase of the maneuver.

* * * * *